US007868009B2

(12) United States Patent  (10) Patent No.: US 7,868,009 B2
Swinnen et al.  (45) Date of Patent: *Jan. 11, 2011

(54) N-HYDROXYAMIDE DERIVATIVES AND USE THEREOF

(75) Inventors: Dominique Swinnen, Beaumont (FR); Jerome Gonzalez, Annemasse (FR)

(73) Assignee: Merck Serono, S.A., Vaud (CH)

( * ) Notice: Subject to any disclaimer, the term of this patent is extended or adjusted under 35 U.S.C. 154(b) by 386 days.

This patent is subject to a terminal disclaimer.

(21) Appl. No.: 11/883,286

(22) PCT Filed: Jan. 27, 2006

(86) PCT No.: PCT/EP2006/050480

§ 371 (c)(1),
(2), (4) Date: Jul. 30, 2007

(87) PCT Pub. No.: WO2006/079653

PCT Pub. Date: Aug. 3, 2006

(65) Prior Publication Data

US 2008/0090838 A1    Apr. 17, 2008

Related U.S. Application Data

(60) Provisional application No. 60/648,931, filed on Feb. 1, 2005.

(30) Foreign Application Priority Data

Jan. 31, 2005    (EP) .................................. 05100646

(51) Int. Cl.
*A61K 31/495* (2006.01)
*C07D 295/185* (2006.01)
*C07D 317/34* (2006.01)
*A61K 31/451* (2006.01)

(52) U.S. Cl. .................. 514/255.01; 544/374; 544/391; 546/207; 546/226; 514/330

(58) Field of Classification Search ........................ None
See application file for complete search history.

(56) References Cited

U.S. PATENT DOCUMENTS 5,540,938 A    7/1996    Masterson et al.

FOREIGN PATENT DOCUMENTS

| EP | 0 627 406 A1 | 12/1994 |
|---|---|---|
| WO | WO 95/33731 A | 12/1995 |
| WO | WO 98/48802 A1 | 11/1998 |
| WO | WO 99/55678 A1 | 11/1999 |
| WO | WO 99/67230 A1 | 12/1999 |
| WO | WO 01/45698 A1 | 6/2001 |
| WO | WO 01/47920 A1 | 7/2001 |
| WO | WO 01/83461 A1 | 11/2001 |
| WO | WO 02/28866 A2 | 4/2002 |
| WO | WO 02/080897 A1 | 10/2002 |
| WO | WO 03/068230 A1 | 8/2003 |
| WO | WO 03/070711 A1 | 8/2003 |
| WO | WO 03/084941 A | 10/2003 |
| WO | WO 2004/028521 A2 | 4/2004 |
| WO | WO 2004/043965 A1 | 5/2004 |
| WO | 2006/010751 A1 * | 2/2006 |

OTHER PUBLICATIONS

Birkedal-Hansen et al. Critical Reviews in Oral Biology and Medicine, vol. 4(2), p. 197-250 (1993).*
Vincenti et al. Arthritis & Rheumatism vol. 17, p. 1115-1126 (1994).*
Matrx Metalloproteinase, from Wikipedia,the free encyclopedia (8 pages), retrieved from the Internet on Dec. 17, 2009 at http://en.wikipedia.org/wiki/Matrix_metalloproteinase.*
Muroski et al. Curr.Pharm.Biotechnol. 9(1),p. 34-46 (2008).*
Belvisi, M., et al., "Review: The Role of Matrix Metalloproteinases (MMPs) in the Pathophysiology of Chronic Obstructive Pulmonary Disease (COPD): A Therapeutic Role for Inhibitors of MMPs?," *Inflammation Research*, 52: 95-100 (2003).
Clark, I., et al., "Metalloproteinases: Their Role in Arthritis and Potential as Therapeutic Targets," *Expert Opin. Ther. Targets*, 7(1): 19-34 (2003).
Doherty, T., et al., "Therapeutic Developments in Matrix Metalloproteinase Inhibition," *Expert Opin. Ther. Patents*, 12(5): 665-707 (2002).
Fingleton, B., "Matrix Metalloproteinase Inhibitors for Cancer Therapy: the Current Situation and Future Prospects," *Expert Opin. Ther. Targets*, 7(3): 385-397 (2003).
Galis, Z., et al., "Matrix Metalloproteinases in Vascular Remodeling and Atherogenesis: The Good, the Bad, and the Ugly," *Circulation Research*, 90: 251-262 (2002).

(Continued)

*Primary Examiner*—Emily Bernhardt
(74) *Attorney, Agent, or Firm*—Hamilton, Brook, Smith & Reynolds, P.C.

(57) ABSTRACT

The present invention is related to N-hydroxyamide derivatives of Formula (I):

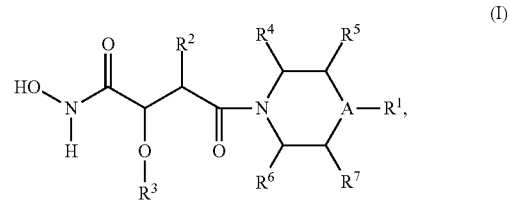

and use thereof in particular for the treatment and/or prophylaxis of autoimmune disorders, inflammatory diseases, cardiovascular diseases, neurodegenerative diseases, cancer, respiratory diseases and fibrosis, including multiple sclerosis, arthritis, emphysema, chronic obstructive pulmonary disease, liver and pulmonary fibrosis.

9 Claims, No Drawings

OTHER PUBLICATIONS

Henrotin, Y., et al., "The Inhibition of Metalloproteinases to Treat Osteoarthritis: Reality and New Perspectives," *Expert Opin. Ther. Patents*, 12(1): 29-43 (2002).

Hooper, N., et al., "Membrane Protein Secretases," *Biochem. J.*, 321: 265-279 (1997).

Horstmann, S., et al., "Profiles of Matrix Metalloproteinases, Their Inhibitors, and Laminin in Stroke Patients," *Stroke*, 34(9): 2165-2172 (2003).

Ingman, T., et al., "Matrix Metalloproteinases and Their Inhibitors in Gingival Crevicular Fluid and Saliva of Periodontitis Patients," *Journal of Clinical Periodontology*, 23: 1127-1132 (1996).

Knight, C., et al., "A Novel Coumarin-labelled Peptide for Sensitive Continuous Assays of the Matrix Metalloproteinases," *Federation of European Biochemical Societies Letters*, 296(3): 263-266 (1992).

Krishna, G., et al., "New Therapies for Chronic Obstructive Pulmonary Disease," *Expert Opin. Investig. Drugs*, 13(3): 255-267 (2004).

Leppert, D., et al., "Matrix Metalloproteinases: Multifunctional Effectors of Inflammation in Multiple Sclerosis and Bacterial Meningitis," *Brain Research Reviews*, 36: 249-257 (2001).

Liu, M., et al., "Association of Increased Expression of Macrophage Elastase (Matrix Metalloproteinase 12) With Rheumatoid Arthritis," *Arthritis & Rheumatism*, 50(10): 3112-3117 (2004).

Makrakis, E., et al., "Matrix Metalloproteinase-9 and Tissue Inhibitor of Metalloproteinase-1 in Plasma/serum and Urine of Women During Term and Threatened Preterm Labor: A Clinical Approach," *The Journal of Maternal-Fetal and Neonatal Medicine*, 14(3): 170-176 (2003).

Opdenakker, G., et al., "Functional Roles and Therapeutic Targeting of Gelatinase B and Chemokines in Multiple Sclerosis," *The Lancet Neurology*, 2: 747-756 (2003).

Peterson, J., "Matrix Metalloproteinase Inhibitor Development and the Remodeling of Drug Discovery," *Heart Failure Reviews*, 9: 63-79 (2004).

Skiles, J., et al., "The Design, Structure, and Therapeutic Application of Matrix Metalloproteinase Inhibitors," *Current Medicinal Chemistry*, 8(4): 425-474 (2001).

Skotnicki, J., et al., "Design Strategies for the Identification of MMP-13 and TACE Inhibitors," *Current Opinion in Drug Discovery & Development*, 6(5): 742-759 (2003).

Visse, R., et al., "Matrix Metalloproteinases and Tissue Inhibitors of Metalloproteinases: Structure, Function, and Biochemistry," *Circulation Research*, 92: 827-839 (2003).

Vos, C., et al., "Matrix Metalloproteinase-12 is Expressed in Phagocytotic Macrophages in Active Multiple Sclerosis Lesions," *Journal of Neuroimmunology*, 138: 106-114 (2003).

Wada, C., et al., "Phenoxyphenyl Sulfone *N*-Formylhydroxylamines (Retrohydroxamates) as Potent, Selective, Orally Bioavailable Matrix Metalloproteinase Inhibitors," *J. Med. Chem.*, 45(1): 219-232 (2002).

International Search Report for International Application No. PCT/EP2006/050480 dated Apr. 21, 2006.

Written Opinion of the International Searching Authority, International Application No. PCT/EP2006/050480 dated Apr. 21, 2006.

Notification Concerning Transmittal of International Preliminary Report on Patentability, and International Preliminary Report on Patentability, International Application No, PCT/EP2006/050480 dated Jul. 31, 2007.

\* cited by examiner

N-HYDROXYAMIDE DERIVATIVES AND USE THEREOF

RELATED APPLICATIONS

This application is the U.S. National Stage of International Application No. PCT/EP2006/050480, filed Jan. 27, 2006, published in English, and claims priority under 35 U.S.C. §119 or 365 to U.S. Provisional Application No. 60/648,931, filed Feb. 1, 2005 and European Application No. 05100646.8 filed Jan. 31, 2005.

FIELD OF THE INVENTION

The present invention is related to N-hydroxyamide derivatives of Formula (I), pharmaceutical composition thereof, process of making thereof and to their use for the treatment and/or prophylaxis of autoimmune disorders and/or inflammatory diseases, cardiovascular diseases, neurodegenerative diseases, cancer, respiratory diseases and fibrosis. Specifically, the present invention is related to N-hydroxyamide derivatives for the modulation, notably the inhibition of the activity or function of matrix metalloproteinases, especially gelatinases and metalloelastase.

BACKGROUND OF THE INVENTION

Metalloproteinases are a superfamily of proteinases (enzymes) named for their dependence on a metal ion (zinc) in the active site.

The matrix metalloproteinases (MMPs) form a metalloproteinase sub-family having as one of major biological function to catalyse the breakdown of connective tissue or extracellular matrix through their ability to hydrolyse various components of the tissue or matrix, such as collagens, gelatins, proteoglycans, fibronectins and elastin.

The matrix metalloproteinase family is further divided according to their function and substrates (Visse al, 2003, *Circ. Res.*, 92, 827-839) and comprises collagenases (MMP-1, MMP-8, MMP-13 and MMP-18), gelatinases (MMP-2 and MMP-9), stromelysins (MMP-3, MMP-10 and MMP-11), membrane-type MMPs (MT-MMP-1 to MT-MMP-6 and MMP-14, MMP-15, MMP-16, MMP-17, MMP-24 and MMP-25), matrilysins (MMP-7 and MMP-26) and other unclassified MMPs such as metalloelastase (MMP-12), enamelysin (MMP-20), epilysin (MMP-28), MMP-19, MMP-22 and MMP-23.

A part from their role in degrading connective tissue, MMPs are involved in the biosynthesis of TNF-alpha and in the post translational proteolysis processing, or shedding of biologically important membrane proteins (Hooper et al., 1997, *Biochem J*, 321, 265-279). MMPs for example contribute to the local growth and spread of malignant lesions and therefore have been a target for anti-tumor drug development (Fingleton et al., 2003, *Expert Opin. Ther. Targets*, 7(3): 385-397). Disorders such as inflammatory disorders like arthritis (Clark et al., 2003, *Expert. Opin. Ther Targets*, 7(1): 19-34 and Liu et al., 2004, *Arthritis and Rheumatism*, 50(10), 3112-3117), respiratory disorders such as emphysema, atherosclerosis (Galis et al., 2002, *Circ. Res.*, 90:251-262), neurological disorders such as degenerative nervous system diseases, multiple sclerosis (Leppert et al., 2001, *Brain Res. Rev.*, 36:249-257), periodontitis (Ingman et al., 1996, *J. Clin. Periodontal.*, 23:1127-1132), pre-term labor (Makrakis et al., 2003, *J. Matern Fetal & Neonatal Medicine*, 14(3): 170-6) and wound healing have been demonstrated to be associated with MMPs expression and/or activity.

A wide variety of matrix metalloproteinase inhibitors (MMPIs) has been developed (Skiles et al., 2001, *Current Medicinal Chemistry*, 8, 425-474; Peterson, 2004, *Heart Failure Reviews*, 9, 63-79; Henrotin et al., 2002, *Expert Opin. Ther. Patents*, 12(1): 29-43). However, many MMPIs exhibit a muscoskeletal syndrome (tendonitis, fibroplasias, mylasia, arthralasia) as a dose-limiting side effect. It has been proposed that inhibition of MMP-1 or MMP-14 may be responsible for these effects.

Therefore, there is an increasing need to develop matrix metalloproteinase inhibitors with a well-defined specificity profile.

Specific inhibitors, especially towards MMP-1, have been reported, including MMP-13 inhibitors (Stotnicki et al., 2003, *Current Opinion in Drug Discovery and Development*, 6(5):742-759), MMP-12 inhibitors (WO 01/83461), MMP-2 and MMP-9 inhibitors (Wada et al., 2002, *J. Biol. Chem.* 45, 219-232).

The high relevance of the metalloproteinase pathway in some widely spread diseases stresses the need to develop inhibitors, including selective inhibitors of MMPs, especially of gelatinases such as MMP-2 and/or MMP-9 and/or MMP-12.

SUMMARY OF THE INVENTION

It is an object of the invention to provide substances which are suitable for the treatment and/or prevention of disorders related to autoimmune disorders and/or inflammatory diseases, cardiovascular diseases, neurodegenerative diseases, stroke, cancer, pre-term labor, endometriosis, respiratory diseases and fibrosis.

It is further an object of the present invention to provide substances which are suitable for the treatment and/or prevention of multiple sclerosis, rheumatoid arthritis, emphysema, chronic obstructive pulmonary disease and fibrosis.

It is notably an object of the present invention to provide chemical compounds which are able to modulate, especially inhibit the activity or function of matrix metalloproteinases, especially gelatinases and elastase in mammals, especially in humans.

It is furthermore an object of the present invention to provide a new category of pharmaceutical formulations for the treatment of and/or diseases mediated selected from autoimmune disorders, inflammatory diseases, cardiovascular diseases, neurodegenerative diseases, stroke, cancer, pre-term labor, endometriosis, respiratory diseases and fibrosis.

It is furthermore an object of the present invention to provide a process for making chemical compounds according to the invention.

It is finally an object of the present invention to provide a method for the treatment and/or prevention of disorders selected from autoimmune disorders, inflammatory diseases, cardiovascular diseases, neurodegenerative diseases, stroke, cancer, pre-term labor, endometriosis, respiratory diseases and fibrosis.

In a first aspect, the invention provides N-hydroxyamide derivatives of Formula (I):

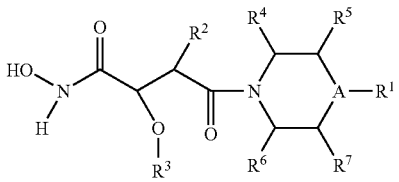

wherein A, $R^1$, $R^2$, $R^3$, $R^4$, $R^5$, $R^6$ and $R^7$ are defined in the detailed description.

In a second aspect, the invention provides a compound according to Formula (I) for use as a medicament.

In a third aspect, the invention provides a use of a compound according to Formula (I) for the preparation of a pharmaceutical composition for the treatment of a disorder selected from autoimmune disorders, inflammatory diseases, cardiovascular diseases, neurodegenerative diseases, stroke, cancer, pre-term labor, endometriosis, respiratory diseases and fibrosis.

In a fourth aspect, the invention provides a pharmaceutical composition comprising at least one a compound according to Formula (I) and a pharmaceutically acceptable carrier, diluent or excipient thereof.

In a fifth aspect, the invention provides a method of treatment comprising the administration of a compound according to Formula (I) in a patient in need thereof. In a sixth aspect, the invention provides a method of synthesis of a compound according to Formula (I).

In a seventh aspect, the invention provides compounds according to Formula (IV):

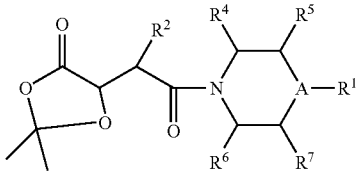

wherein A, $R^1$, $R^2$, $R^4$, $R^5$, $R^6$ and $R^7$ are defined in the detailed description.

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

The term "MMPs" refers to "matrix metalloproteinases". For recent reviews of MMPs, see Visse et al., 2003 above; Fingleton et al., 2003, above; Clark et al., 2003, above and Doherty et al., 2002, *Expert Opinion Therapeutic Patents* 12(5): 665-707.

Illustrative but not limiting examples of such MMPs are:

Collagenases: usually associated with diseases linked to breakdown of collagen-based tissue e.g. rheumatoid arthritis and osteoarthritis:

MMP-1 (also known as collagenase 1, or fibroblast collagenase), substrates collagen I, collagen II, collagen III, gelatin, proteoglycans. Over-expression of this enzyme is believed to be associated with emphysema, with hyperkeratosis and atherosclerosis, overexpressed alone in papillary carcinoma.

MMP-8 (also known as collagenase 2, or neutrophil collagenase), substrates collagen I, collagen II, collagen III, collagen V, collagen VII, collagen IX, gelatin over-expression of which can lead to non-healing chronic ulcers.

MMP-13 (also known as collagenase 3), substrates collagen I, collagen II, collagen III, collagen IV, collagen IX, collagen X, collagen XIV, fibronectin, gelatin, recently identified as being over-expressed alone in breast carcinoma and involved in rheumatoid arthritis.

Stromelysins:

MMP-3 (also known as stromelysin I), substrates collagen III, collagen IV, collagen V, collagen IX, collagen X, laminin, nidogen, over-expression believed to be involved in atherosclerosis, aneurysm and restenosis.

Gelatinases—inhibition believed to exert a favorable effect on cancer, in particular invasion and metastasis.

MMP-2 (also known as gelatinase A, 72 kDa gelatinase, basement membrane collagenase, or proteoglycanase), substrates Collagen I, Collagen II, Collagen IV, Collagen V, Collagen VII, Collagen X, Collagen XI, collagen XIV, elastin, fibronectin, gelatin, nidogen, believed to be associated with tumor progression through specificity for type IV Collagen (high expression observed in solid tumors and believed to be associated with their ability to grow, invade, develop new blood vessels and metastasize) and to be involved in acute lung inflammation and in respiratory distress syndrome (Krishna et al., 2004, *Expert Opin. Invest. Drugs*, 13(3):255-267).

MMP-9 (also known as gelatinase B, or 92 kDa gelatinase), substrates Collagen I, Collagen III, Collagen IV, Collagen V, Collagen VII, collagen X, Collagen XIV, elastin, fibronectin, gelatin, nidogen. The above enzyme is believed to be associated with tumor progression through specificity for type IV Collagen, to be released by eosinophils in response to exogenous factors such as air pollutants, allergens and viruses, to be involved in the inflammatory response in multiple sclerosis (Opdenakker et al., 2003, *The Lancet Neurology*, 2, 747-756) and asthma and to be involved in acute lung inflammation, respiratory distress syndrome, chronic obstructive pulmonary disorder (COPD) and/or asthma (Krishna et al., 2004, above). MMP-9 is also thought to be involved in stroke (Horstmann et al., 2003, *Stroke* 34(9), 2165-70).

Unclassified MMPs:

MMP-12 (also known as metalloelastase, human macrophage elastase, or HME), substrates fibronectin, larninin, believed to play a role in tumour growth inhibition and regulation of inflammation such as multiple sclerosis (Vos et al., 2003, *Journal of Neuroimmunology*, 138, 106-114) and to play a pathological role in emphysema, COPD (Belvisi et al., 2003, *Inflamm. Res.*, 52; 95-100) and in atherosclerosis, aneurysm and restenosis.

The expression "MMP-associated disorder" refers to a disorder which is treatable according to the invention and that encompasses all disorders in which the expression and/or activity of at least one MMP needs to be decreased irrespective of the cause of such disorders. Such disorders include, for example, those caused by inappropriate extracellular matrix (ECM) degradation.

Illustrative but not limiting examples of such MMP-associated disorders are:

Cancer such as breast cancer and solid tumors; inflammatory disorders such as for example inflammatory bowel diseases and neuroinflammation such as multiple sclerosis; lung diseases such as chronic obstructive pulmonary disorder (COPD), emphysema, asthma, acute lung injury, and acute respiratory distress syndrome; dental diseases such as periodontal disease and gingivitis; joint and bone diseases such as osteoarthritis and rheumatoid arthritis; liver diseases such as liver fibrosis, cirrhosis and chronic liver disease; fibrotic diseases such as pulmonary fibrosis, pancreatitis, lupus, glomerulosclerosis, systemic sclerosis skin fibrosis, post-radiation fibrosis and cystic fibrosis; vascular pathologies such as aortic aneurysm, atherosclerosis, hypertension, cardiomyopathy and myocardial infarction; restenosis; opthalmological disorders such as diabetic retinopathy, dry eye syndrome, macula degeneration and corneal ulceration and degenerative diseases of the central nervous system such as amyotrophic lateral sclerosis.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like. By analogy, "$C_1$-$C_{12}$-alkyl" refers to monovalent alkyl groups having 1 to 12 carbon atoms, including "$C_1$-$C_6$-alkyl" groups and heptyl, octyl, nonyl, decanoyl, undecanoyl and dodecanoyl groups and "$C_1$-$C_{10}$-alkyl" refers to monovalent alkyl groups having 1 to 10 carbon atoms, "$C_1$-$C_8$-alkyl" refers to monovalent alkyl groups having 1 to 8 carbon atoms and "$C_1$-$C_5$-alkyl" refers to monovalent alkyl groups having 1 to 5 carbon atoms.

"Heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl.

"Aryl" refers to an unsaturated aromatic carbocyclic group of from 6 to 14 carbon atoms having a single ring (e.g., phenyl) or multiple condensed rings (e.g., naphthyl). Aryl include phenyl, naphthyl, phenantrenyl and the like.

"$C_1$-$C_6$-alkyl aryl" refers to aryl groups having a $C_1$-$C_6$-alkyl substituent, including methyl phenyl, ethyl phenyl and the like.

"Aryl $C_1$-$C_6$-alkyl" refers to $C_1$-$C_6$-alkyl groups having an aryl substituent, including 3-phenylpropanoyl, benzyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to heteroaryl groups having a $C_1$-$C_6$-alkyl substituent, including methyl furyl and the like.

"Heteroaryl $C_1$-$C_6$-alkyl" refers to $C_1$-$C_6$-alkyl groups having a heteroaryl substituent, including furyl methyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"$C_2$-$C_6$-alkenyl aryl" refers to an aryl groups having a $C_2$-$C_6$-alkenyl substituent, including vinyl phenyl and the like.

"Aryl $C_2$-$C_6$-alkenyl" refers to a $C_2$-$C_6$-alkenyl groups having an aryl substituent, including phenyl vinyl and the like.

"$C_2$-$C_6$-alkenyl heteroaryl" refers to heteroaryl groups having a $C_2$-$C_6$-alkenyl substituent, including vinyl pyridinyl and the like.

"Heteroaryl $C_2$-$C_6$-alkenyl" refers to $C_2$-$C_6$-alkenyl groups having a Heteroaryl substituent, including pyridinyl vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidine, piperidine, piperazine, morpholine, tetrahydrofurane and the like.

"$C_1$-$C_6$-alkyl cycloalkyl" refers to $C_3$-$C_8$-cycloalkyl groups having a $C_1$-$C_6$-alkyl substituent, including methyl cyclopentyl and the like.

"Cycloalkyl $C_1$-$C_6$-alkyl" refers to $C_1$-$C_6$-alkyl groups having a $C_3$-$C_8$-cycloalkyl substituent, including 3-cyclopentyl propyl and the like.

"$C_1$-$C_6$-alkyl heterocycloalkyl" refers to heterocycloalkyl groups having a $C_1$-$C_6$-alkyl substituent, including 1-methylpiperazine and the like.

"Heterocycloalkyl $C_1$-$C_6$-alkyl" refers to $C_1$-$C_6$-alkyl groups having a heterocycloalkyl substituent, including 4-methyl piperidyl and the like.

"Carboxy" refers to the group —C(O)OH.

"Carboxy $C_1$-$C_6$-alkyl" refers to $C_1$-$C_6$-alkyl groups having an carboxy substituent, including 2-carboxyethyl and the like.

"Acyl" refers to the group —C(O)R where R includes "$C_1$-$C_{12}$-alkyl", preferably "$C_1$-$C_6$-alkyl", "aryl", "heteroaryl", "$C_3$-$C_8$-cycloalkyl", "heterocycloalkyl", "aryl $C_1$-$C_6$-alkyl", "heteroaryl $C_1$-$C_6$-alkyl", "$C_3$-$C_8$-cycloalkyl $C_1$-$C_6$-alkyl" or "heterocycloalkyl $C_1$-$C_6$-alkyl".

"Acyl $C_1$-$C_6$-alkyl" to $C_1$-$C_6$-alkyl groups having an acyl substituent, including acetyl, 2-acetylethyl and the like.

"Acyl aryl" refers to aryl groups having an acyl substituent, including 2-acetylphenyl and the like.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acyloxy $C_1$-$C_6$-alkyl" refers to $C_1$-$C_6$-alkyl groups having an acyloxy substituent, including propionic acid ethyl ester and the like.

"Alkoxy" refers to the group —O—R where R includes "$C_1$-$C_6$-alkyl" or "aryl" or "hetero-aryl" or "aryl $C_1$-$C_6$-alkyl" or "heteroaryl $C_1$-$C_6$-alkyl". Preferred alkoxy groups include for example, methoxy, ethoxy, phenoxy and the like.

"Alkoxy $C_1$-$C_6$-alkyl" refers to alkoxy groups having an $C_1$-$C_6$-alkyl substituent, including methoxy, methoxyethyl and the like.

"Alkoxycarbonyl" refers to the group —C(O)OR where R includes H, "$C_1$-$C_6$-alkyl" or "aryl" or "heteroaryl" or "aryl $C_1$-$C_6$-alkyl" or "heteroaryl $C_1$-$C_6$-alkyl" or "heteroalkyl".

"Alkoxycarbonyl $C_1$-$C_6$-alkyl" refers to $C_1$-$C_5$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "aryl $C_1$-$C_6$-alkyl" or "heteroaryl $C_1$-$C_6$-alkyl", including N-phenyl formamide.

"Aminocarbonyl $C_1$-$C_6$-alkyl" refers to $C_1$-$C_6$-alkyl groups having an aminocarbonyl substituent, including 2-(dimethylaminocarbonyl)ethyl, N-ethyl acetamide, N,N-Diethyl-acetamide and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acylamino $C_1$-$C_6$-alkyl" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl", and where R' and R", together with the nitrogen atom to which they are attached, can optionally form a 3-8-membered heterocycloalkyl ring.

"Ureido $C_1$-$C_6$-alkyl" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Amino" refers to the group —NRR' where each R,R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Amino $C_1$-$C_6$-alkyl" refers to $C_1$-$C_5$-alkyl groups having an amino substituent, including 2-(1-pyrrolidinyl)ethyl and the like.

"Ammonium" refers to a positively charged group —N$^+$RR'R", where each R,R',R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Ammonium $C_1$-$C_6$-alkyl" refers to $C_1$-$C_6$-alkyl groups having an ammonium substituent, including 1-ethylpyrrolidinium and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyloxy $C_1$-$C_6$-alkyl" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyl $C_1$-$C_6$-alkyl" refers to $C_1$-$C_5$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., a —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfinyl $C_1$-$C_6$-alkyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., a —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "alkynylheteroaryl $C_2$-$C_6$", "cycloalkyl $C_1$-$C_6$-alkyl", "heterocycloalkyl $C_1$-$C_6$-alkyl". Preferred sulfanyl groups include methylsulfanyl, ethylsulfanyl, and the like.

"Sulfanyl $C_1$-$C_6$-alkyl" refers to $C_1$-$C_5$-alkyl groups having a sulfanyl substituent, including 2-(ethylsulfanyl)ethyl and the like.

"Sulfonylamino" refers to a group —NRSO$_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonylamino $C_1$-$C_6$-alkyl" refers to $C_1$-$C_6$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl C$_2$-C$_6$-alkenyl", "aryl C$_2$-C$_6$-alkynyl", "heteroaryl C$_2$-C$_6$-alkynyl", "cycloalkyl C$_1$-C$_6$-alkyl", "heterocycloalkyl C$_1$-C$_6$-alkyl".

"Aminosulfonyl C$_1$-C$_6$-alkyl" refers to C$_1$-C$_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkenyl", "alkynyl", "aryl", "heteroaryl", "cycloalkyl", "heterocycloalkyl" etc. groups can optionally be substituted with from 1 to 5 substituents selected from the group consisting of "C$_1$-C$_6$-alkyl", "C$_2$-C$_6$-alkenyl", "C$_2$-C$_6$-alkynyl", "cycloalkyl", "heterocycloalkyl", "aryl C$_1$-C$_6$-alkyl", "heteroaryl C$_1$-C$_6$-alkyl", "cycloalkyl C$_1$-C$_6$-alkyl", "heterocycloalkyl C$_1$-C$_6$-alkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like.

"Pharmaceutically acceptable salts or complexes" refers to salts or complexes of the below-specified compounds of Formula (I). Examples of such salts include, but are not restricted, to base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. Said prodrug is comprised of the active drug compound itself and a chemical masking group. Such masking group may be a cyclic acetonide of formula (I') wherein Y is a methyl or a hydrogen, and Y' is methyl, C$_2$-C$_4$ alkyl, phenyl, benzyl, optionally substituted with one to three substituents selected from C$_1$-C$_4$ alkyl, C$_1$-C$_4$ alkoxy, hydroxy, amino, methylamino, dimethylamino, chloro and fluoro; A, R$^1$, R$^2$, R$^4$, R$^5$, R$^6$ and R$^7$ are defined in the detailed description.

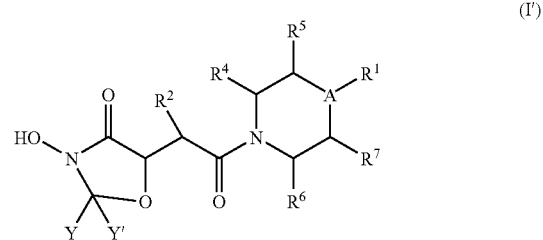

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

An "interferon" or "IFN", as used herein, is intended to include any molecule defined as such in the literature, comprising for example any types of IFNs mentioned in the above section "Background of the Invention". In particular, IFN-α, IFN-β and IFN-γ are included in the above definition. IFN-β is the preferred IFN according to the present invention. IFN-β suitable in accordance with the present invention is commercially available e.g. as Rebif® (Serono), Avonex® (Biogen) or Betaferon® (Schering).

The term "interferon-beta (IFN-beta or IFN-β)", as used herein, is intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments. Preferably, IFN-beta is intended to mean recombinant Interferon beta-1a.

IFN-β suitable in accordance with the present invention is commercially available e.g. as Rebif® (Serono), Avonex® (Biogen) or Betaferon® (Schering). The use of interferons of human origin is also preferred in accordance with the present invention. The term interferon, as used herein, is intended to encompass salts, functional derivatives, variants, analogs and active fragments thereof.

Rebif® (recombinant interferon-β) is the latest development in interferon therapy for multiple sclerosis (MS) and represents a significant advance in treatment. Rebif® is interferon (IFN)-beta 1a, produced from mammalian cell lines. It was established that interferon beta-1a given subcutaneously three times per week is efficacious in the treatment of Relapsing-Remitting Multiple Sclerosis (RRMS). Interferon beta-1a can have a positive effect on the long-term course of MS by reducing number and severity of relapses and reducing the burden of the disease and disease activity as measured by MRI.

The dosing of IFN-β in the treatment of relapsing-remitting MS according to the invention depends on the type of IFN-β used.

In accordance with the present invention, where IFN is recombinant IFN-β1b produced in *E. Coli*, commercially available under the trademark Betaseron®, it may preferably be administered sub-cutaneously every second day at a dosage of about of 250 to 300 μg or 8 MIU to 9.6 MIU per person.

In accordance with the present invention, where IFN is recombinant IFN-β1a, produced in Chinese Hamster Ovary cells (CHO cells), commercially available under the trademark Avonex®, it may preferably be administered intramuscularly once a week at a dosage of about of 30 μg to 33 μg or 6 MIU to 6.6 MIU per person.

In accordance with the present invention, when IFN is recombinant IFN-β1a, produced in Chinese Hamster Ovary cells (CHO cells), commercially available under the trademark Rebif®, it may preferably be administered sub-cutaneously three times a week (TIW) at a dosage of 22 to 44 μg or 6 MIU to 12 MIU per person.

Compounds according to the present invention also comprise pharmaceutically acceptable salts thereof. Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

It has now been found that compounds of the present invention are modulators of the matrix metalloproteinases, especially gelatinases and elastase, including MMP-2 and/or MMP-9 and/or MMP-12. When the matrix metalloproteinase enzyme is inhibited by the compounds of the present invention, the inhibited MMP(s) is (are) unable to exert its enzymatic, biological and/or pharmacological effects. The compounds of the present invention are therefore useful in the treatment and prevention of autoimmune disorders and/or inflammatory diseases, cardiovascular diseases, preterm labor, endometriosis, neurodegenerative diseases, stroke, cancer, respiratory diseases and fibrosis.

In one embodiment, the invention provides derivatives of Formula (I)

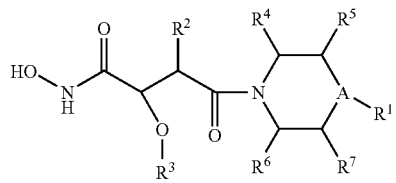

wherein:

A is selected from —C(B)— and N;

B is H or B forms a bond with either $R^5$ or $R^7$;

$R^1$ is selected from H; optionally substituted $C_1$-$C_6$ alkyl; optionally substituted $C_2$-$C_6$ alkenyl; optionally substituted $C_2$-$C_6$ alkynyl;

optionally substituted $C_3$-$C_8$-cycloalkyl, including cyclohexyl;

optionally substituted heterocycloalkyl;

optionally substituted aryl, including optionally substituted phenyl such as phenyl, fluorophenyl (e.g. 2-fluorophenyl, 4-fluorophenyl, 3-chlorophenyl), chlorophenyl (e.g. 2-chlorophenyl, 4-chlorophenyl), methoxy phenyl (e.g. 4-methoxyphenyl), ethoxy phenyl (e.g. 4-ethoxyphenyl), cyanophenyl (e.g. 2-cyanophenyl), trifluoromethyl phenyl (e.g. 4-trifluoromethoxy phenyl), biphenyl (e.g. 4-biphenyl) and 4-chloro-2-fluorophenyl, 2-fluoro-5-methoxyphenyl;

optionally substituted heteroaryl, including optionally substituted pyridinyl, such as pyridinyl, methyl pyridinyl (e.g. 4-methylpyridin-2-yl, 6-methylpyridin-2-yl), chloro pyridinyl (e.g. 6-chloropyridin-2-yl, 5-chloropyridin-2-yl, 3,5-dichloropyridin-4-yl), trifluoromethyl pyridinyl (e.g. 3-(trifluoromethyl)pyridin-2-yl, 4-(trifluoromethyl)pyridin-2-yl, 5-(trifluoro methyl)pyridin-2-yl), cyano pyridinyl (e.g. 5-cyanopyridin-2-yl), phenyl pyridinyl (e.g. 5-phenyl pyridin-2-yl) and optionally substituted fused pyridinyl (e.g. 4-[6-methyl-2-(trifluoromethyl)quinolin-4-yl]); including optionally substituted pyrazinyl (e.g. 4-pyrazin-2-yl); including optionally substituted thiadiazolyl such as such as 3-phenyl thiadiazolyl (e.g. 3-phenyl-1,2,4-thiadiazolyl-5-yl); including optionally substituted pyrimidinyl (e.g. 4-pyrimidinyl-2-yl); including optionally substituted oxadiazolyl such as 5-phenyl-1,2,4-oxadiazol-3-yl, 4-pyridin-4-yl-1,2,4-oxadiazol-3-yl and 5-(4-fluorophenyl)-1,3,4-oxadiazol-2-yl;

optionally substituted $C_3$-$C_8$-cycloalkyl $C_1$-$C_6$ alkyl;

optionally substituted heterocycloalkyl $C_1$-$C_6$ alkyl, including 2-morpholin-4-ylethyl;

optionally substituted heteroaryl $C_1$-$C_6$ alkyl, including 2-thienyl ethyl;

optionally substituted amino, including optionally substituted phenyl amino (e.g. phenyl amino, 3-methoxyphenyl amino, 3-(dimethylamino)phenyl amino, 4-ethoxyphenyl amino), heteroaryl amino (e.g. 4-trifluoromethyl)pyrimidin-2-yl, 3-aminopyridin-2-yl); and optionally substituted alkoxy, including 4-(pyridin-2-yloxy), 4-(trifluoromethyl)phenoxy, 2-chlorophenoxy;

$R^2$ is H;

$R^3$ is selected from H, optionally substituted $C_1$-$C_6$ alkyl, optionally substituted $C_2$-$C_6$ alkenyl and optionally substituted $C_2$-$C_6$ alkynyl;

$R^4$, $R^5$, $R^6$ and $R^7$ are independently selected from H; optionally substituted $C_1$-$C_6$ alkyl, including methyl; optionally substituted $C_2$-$C_6$ alkenyl; optionally substituted $C_2$-$C_6$ alkynyl; or $R^4$ and $R^7$ can form together a —CH$_2$— linkage for example to form with the piperazine ring a 2,5-diazabicyclo[2.2.1]hept-2-yl ring;

as well optically active forms as enantiomers, diastereomers and its racemate forms, as well as pharmaceutically acceptable salts thereof.

In a preferred embodiment, the invention provides derivatives of Formula (I) wherein $R^1$ is selected from optionally substituted aryl and optionally substituted heteroaryl.

In a further preferred embodiment, the invention provides derivatives of Formula (I) wherein $R^1$ is optionally substituted aryl such as optionally substituted phenyl, including fluorophenyl (e.g. 4-fluorophenyl), methoxy phenyl (e.g. 4-trifluoromethoxy phenyl) and biphenyl (e.g. 4-biphenyl-4-yl).

In another preferred embodiment, the invention provides derivatives of Formula (I) wherein $R^3$ is H.

In another preferred embodiment, the invention provides derivatives of Formula (I) wherein $R^5$, $R^6$ and $R^7$ are H.

In another preferred embodiment, the invention provides derivatives of Formula (I) wherein $R^4$ is selected from H and optionally substituted $C_1$-$C_6$ alkyl, including methyl.

In a further embodiment, the invention provides derivatives of Formula (I) wherein $R^4$ is H.

In a further embodiment, the invention provides derivatives of Formula (I) wherein $R^4$ is methyl.

In another preferred embodiment, the invention provides derivatives of Formula (I) wherein A is N.

In another preferred embodiment, the invention provides derivatives of Formula (I) wherein $R^1$ is optionally substituted aryl, including optionally substituted phenyl; $R^3$, $R^5$, $R^6$ and $R^7$ are H; $R^4$ is selected from H and methyl; A is N.

Compounds of the present invention include in particular those selected from the following group:

(2R)-4-[4-(4-fluorophenyl)piperazin-1-yl]-N,2-dihydroxy-4-oxobutanamide;

(2S)-4-[4-(4-fluorophenyl)piperazin-1-yl]-N,2-dihydroxy-4-oxobutanamide;

(2S)—N,2-dihydroxy-4-{(2R)-2-methyl-4-[4-(trifluoromethoxy)phenyl]piperazin-1-yl}-4-oxobutanamide;

(2S)-4-[(2R)-4-biphenyl-4-yl-2-methylpiperazin-1-yl]-N,2-dihydroxy-4-oxobutanamide.

In another embodiment of the invention, are provided N-hydroxyamide derivatives according to Formula (I) for use as a medicament.

In another embodiment of the invention, is provided a pharmaceutical composition comprising at least one N-hydroxyamide derivative according to the invention and a pharmaceutically acceptable carrier, diluent or excipient thereof.

In another embodiment of the invention, is provide a use of N-hydroxyamide derivatives according to Formula (I) for the preparation of a medicament for the prophylaxis and/or treatment of a disorder selected from autoimmune disorders, inflammatory diseases, stroke, cardiovascular diseases, neurodegenerative diseases, cancer, pre-term labor, endometriosis, respiratory diseases and fibrosis, including multiple sclerosis, inflammatory bowel disease, rheumatoid arthritis, emphysema, chronic obstructive pulmonary disease (COPD), liver and fibrosis, including liver and pulmonary, pancreatic fibrosis and liver fibrosis In another embodiment of the invention, is provided a use of N-hydroxyamide derivatives according to Formula (I) for the preparation of a pharmaceutical formulation for the modulation, in particular for the inhibition, of the matrix metalloproteinase activity. Particularly, is provided a use according to the invention wherein said matrix metalloproteinase is selected from MMP-2, MMP-9 and MMP-12. Preferably, compounds according to the invention are selective inhibitors of metalloproteineases selected from MMP-2, MMP-9 and/or MMP-12 over MMP-1.

In another embodiment, the invention provides a method of treatment and/or prophylaxis of a disease comprising the administration of a compound according to Formula (I), in a patient in need thereof and wherein the disease is selected from autoimmune disorders, inflammatory diseases, cardiovascular diseases, pre-term labor, endometriosis, neurodegenerative diseases, stroke, cancer, respiratory diseases and fibrosis, including multiple sclerosis, rheumatoid arthritis, emphysema, chronic obstructive pulmonary disease (COPD) and fibrosis, including liver and fibrosis, including pulmonary, pancreatic and liver fibrosis.

In another embodiment, the invention provides a process for the preparation of a N-hydroxyamide derivative according to the invention, comprising the step of reacting a compound of Formula (IV) with a derivative H$_2$NO—R$^8$:

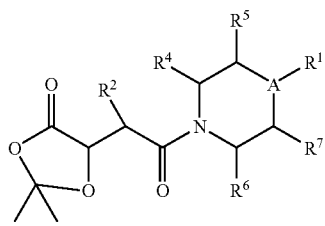

(IV)

wherein A, R$^1$, R$^2$, R$^4$, R$^5$, R$^6$ and R$^7$ are defined above and R$^8$ is selected from H and a protective group such as t-butyl, benzyl, trialkylsilyl, tetrahydropyranyl.

In a further embodiment, the invention provides a process for the preparation of a N-hydroxyamide derivative according to the invention, optionally further comprising a deprotection step (R$^8$ removal, when R$^8$ is not H).

In another embodiment, the invention provides a compound according to Formula (IV):

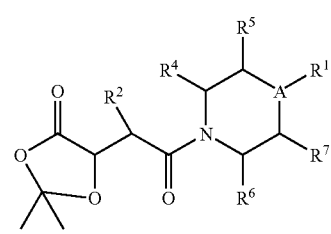

(IV)

wherein A, R$^1$, R$^2$, R$^4$, R$^5$, R$^6$ and R$^7$ are defined above.

In a further embodiment, the invention provides a compound according to Formula (IV) selected from the group:

(5R)-5-{2-[4-(4-fluorophenyl)piperazin-1-yl]-2-oxoethyl}-2,2-dimethyl-1,3-dioxolan-4-one;

(5S)-5-{2-[4-(4-fluorophenyl)piperazin-1-yl]-2-oxoethyl}-2,2-dimethyl-1,3-dioxolan-4-one;

(5S)-2,2-dimethyl-5-[2-((2R)-2-methyl-4-{4-[(trifluoromethyl)oxy]phenyl}piperazin-1-yl)-2-oxoethyl]-1,3-dioxolan-4-one;

(5S)-5-{2-[(2R)-4-biphenyl-4-yl-2-methylpiperazin-1-yl]-2-oxoethyl}-2,2-dimethyl-1,3-dioxolan-4-one;

The compounds of invention have been named according the standards used in the program "ACD/Name" from Advanced Chemistry Development Inc., ACD/Labs (7.06 Release).

The compounds of Formula (I) are useful for the treatment and/or prophylaxis of autoimmune disorders, inflammatory diseases, cardiovascular diseases, pre-term labor, endometriosis, neurodegenerative diseases, stroke, cancer, preterm labor, endometriosis, respiratory diseases and fibrosis, including multiple sclerosis, rheumatoid arthritis, emphysema, chronic obstructive pulmonary disease and fibrosis, including liver and fibrosis, including pulmonary, pancreatic and liver fibrosis.

In another embodiment, the compounds of the invention can be used in the treatment of autoimmune diseases, especially demyelinating diseases such as multiple sclerosis, alone or in combination with a co-agent useful in the treatment of autoimmune diseases, wherein the co-agent is for example selected from the following compounds:

(a) Interferons, e.g. pegylated or non-pegylated interferons, e.g. administered by subcutaneous, intramuscular or oral routes, preferably interferon beta;

(b) Glatiramer, e.g. in the acetate form;

(c) Immunosuppressants with optionally antiproliferative/antineoplastic activity, e.g. mitoxantrone, methotrexate, azathioprine, cyclophosphamide, or steroids, e.g. methylprednisolone, prednisone or dexamethasone, or steroid-secreting agents, e.g. ACTH;

(d) Adenosine deaminase inhibitors, e.g. Cladribine;

(e) Inhibitors of VCAM-1 expression or antagonists of its ligand, e.g. antagonists of the α4/β1 integrin VLA-4 and/or alpha-4-beta-7 integrins, e.g. natalizumab (ANTEGRENO).

Further co-agents such as anti-inflammatory agents (in particular for demyelinating diseases such as multiple sclerosis) are described below:

A further anti-inflammatory agent is Teriflunomide which is described in WO 02/080897

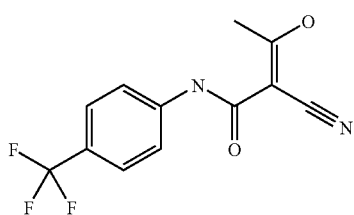

Still a further anti-inflammatory agent is Fingolimod which is described in EP-727406, WO 2004/028251 and WO 2004/028251.

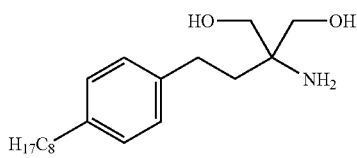

Still a further anti-inflammatory agent is Laquinimod which is described in WO 99/55678.

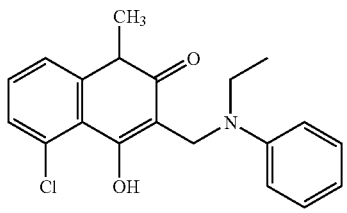

Still a further anti-inflammatory agent is Tensirolimus which is described in WO 02/28866.

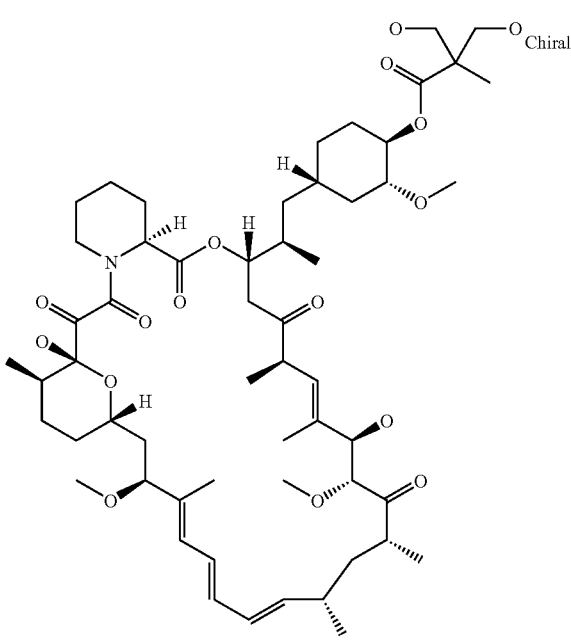

Still a further anti-inflammatory agent is Xaliprodene which is described in WO 98/48802.

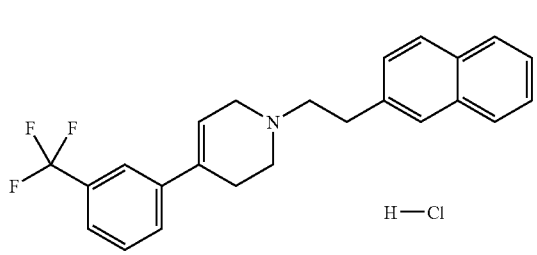

Still a further anti-inflammatory agent is Deskar Pirfenidone which is described in WO 03/068230.

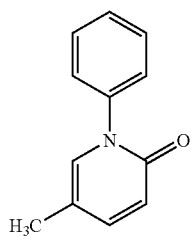

Still a further anti-inflammatory agent is the below benzothiazole derivative which is described in WO 01/47920.

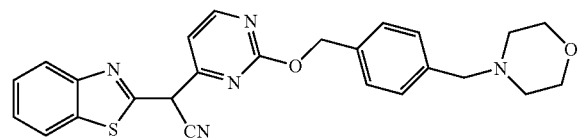

Still a further anti-inflammatory agent is one of the hydroxamic acid derivatives described in WO 03/070711.

Still a further anti-inflammatory agent is MLN3897 which is described in WO 2004/043965.

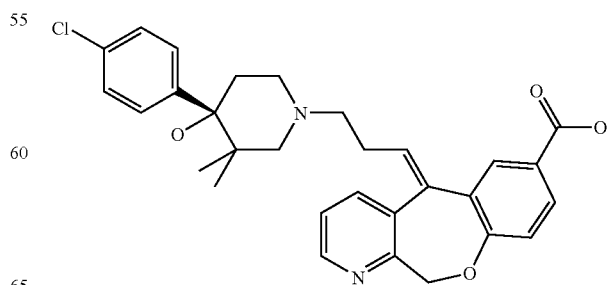

Still a further anti-inflammatory agent is CDP323 which is described in WO 99/67230.

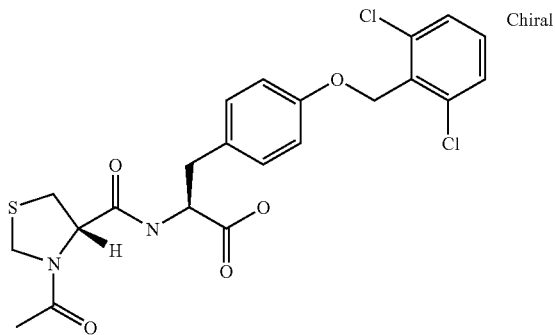

Still a further anti-inflammatory agent is Simvastatin which is described in WO 01/45698.

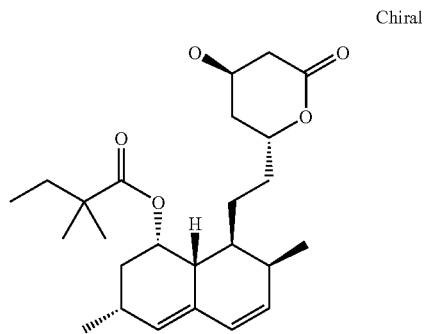

Still a further anti-inflammatory agent is Fampridine which is described in U.S. Pat. No. 5,540,938.

Compounds according to the present invention also comprise its tautomers, its geometrical isomers, its optically active forms as enantiomers, diastereomers and its racemate forms, as well as pharmaceutically acceptable salts thereof. Preferred pharmaceutically acceptable salts of the Formula (VI) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

The derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

When employed as pharmaceuticals, the compounds of the present invention are typically administered in the form of a pharmaceutical composition. Hence, pharmaceutical compositions comprising a compound of the invention and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing a compound of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the derivative of the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the N-hydroxyamide derivatives of Formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20th Edition, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharmaceutical Sciences*.

Synthesis of Compounds of the Invention:

The novel derivatives according to Formula (I) can be prepared from readily available starting materials by several synthetic approaches, using both solution-phase and solid-phase chemistry protocols. Examples of synthetic pathways for the will be described.

The following abbreviations refer respectively to the definitions below:

aq (aqueous), eq (equivalent), h (hour), g (gram), i.p. (intraperitoneal), L (liter), mg (milligram), MHz (Megahertz), min. (minute), mm (millimeter), μm (micrometer), mmol (millimole), mM (millimolar), m.p. (melting point), mL (milliliter), μL (microliter), p.o. (per os), s.c. (sub-cutaneous), BINAP (2,2'-bis(diphenylphosphino)-1,1'-binaphthalene), CDCl$_3$ (deuterated chloroform), CH$_3$CN (Acetonitrile), c-hex (Cyclohexane), DCC (dicyclohexyl carbodiimide), DCM (Dichloromethane), DIC (Diisopropyl carbodiimide), DIEA (Diisopropylethyl-amine), DMF (Dimethylformamide), DMSO (Dimethyl sulfoxide), DMSO-d$_6$ (Deuterated dimethylsulfoxide), EDC (1-(3-Dimethyl-amino-propyl)-3-ethylcarbodiimide), ESI (Electro-spray ionization), Et$_2$O (Diethyl ether), HATU (Dimethylamino-([1,2,3]triazolo[4,5-b]pyridin-3-yloxy)-methylene]-dimethyl-ammonium hexafluoro phosphate), HPLC (High Performance Liquid Chromatography), i-PrOH (2-propanol), LC (Liquid Chromatography), MeOH (Methanol), MS (mass spectrometry), MTBE (Methyl tert-butyl ether), NMM (N-methyl morpholine), NMR (Nuclear Magnetic Resonance), RT (room temperature), PyBOP® (Benzotriazole-1-yl-oxy-tris-pyrrolidino-phosphonium hexafluoro phosphate), Rt (retention time), TBTU (2-(1-H-benzotriazole-1-yl)-1,1,3,3-tetramethyl uromium tetrafluoro borate), TEA (Triethylamine), TFA (Trifluoro acetic acid), THF (Tetrahydrofuran), THP (Tetrahydropyranyl), TLC (Thin Layer Chromatography), UV (Ultraviolet).

Synthetic Approaches:

A preferred process for preparing a compound of Formula (I) consists in coupling a dioxolane-protected di-carboxylic acid of formula (II) with the appropriate amine (III) to form the intermediate (IV) wherein A, R$^1$, R$^2$, R$^4$, R$^5$, R$^6$ and R$^7$ are defined as above (Scheme 1 below). General protocols for such coupling are given below in the Examples, using conditions and methods well known to those skilled in the art to prepare an amide bond from an amine and a carboxylic acid or carboxylic acid derivative (e.g. acyl chloride), with or without standard coupling agents, such as e.g. DIC, EDC, TBTU, DCC, HATU, PyBOP®, Isobutyl chloroformate, 1-methyl-2-chloropyridinium iodide (Mukaiyama's reagent) or others in the presence or not of bases such as TEA, DIEA, NMM in a suitable solvent such as DCM, THF or DMF.

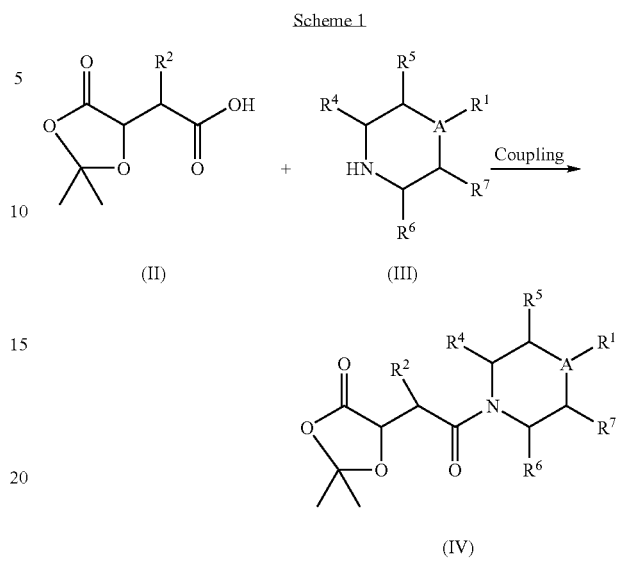

Compounds of formula (III) are commercially available or can be obtained from protocols herein described.

Intermediate of formula (IV) can be reacted with a hydroxylamine or with a protected hydroxylamine H$_2$NO—R$^8$ where R$^8$ is a protecting group such as t-butyl, benzyl, trialkylsilyl or any suitable protecting group, followed by a known deprotection step to form compound of Formula (I) (Scheme 2 below).

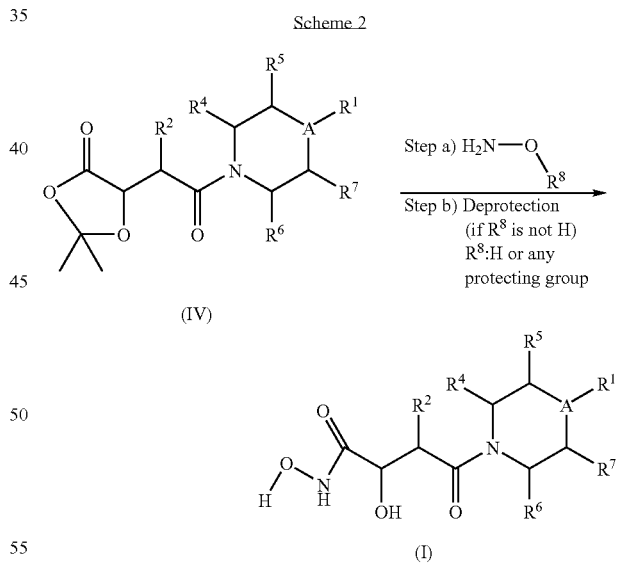

Intermediates of formula (II) may be prepared by methods known or by protocols herein described.

An alternative route for the preparation of compounds of Formula (I) may be the coupling of a carboxylic acids of formula (V) with hydroxylamine or with a protected hydroxylamine H$_2$NO—R$^8$ where R$^8$ is a protecting group such as t-butyl, benzyl, trialkylsilyl, tetrahydropyranyl (THP) or any suitable protecting group, with or without standard coupling agents, such as e.g. DIC, EDC, TBTU, DCC, HATU, PyBOP®, Isobutyl chloroformate, 1-methyl-2-chloropyridinium iodide (Mukaiyama's reagent), followed by a known deprotection step to form compound of Formula (I) (Scheme 3 below).

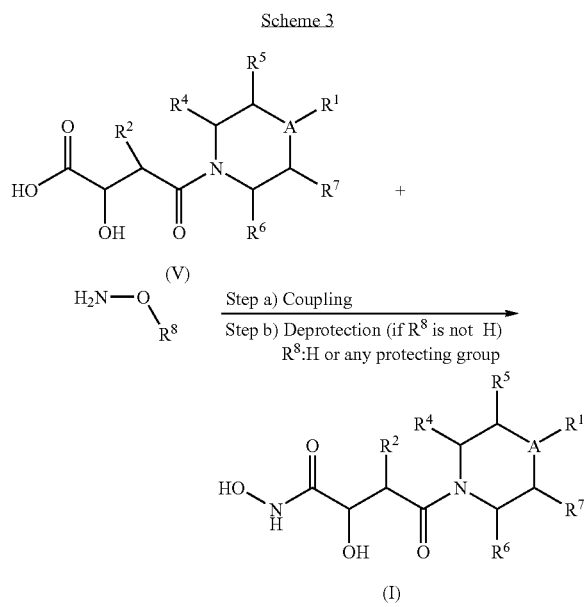

Scheme 3

The HPLC data provided in the examples described below were obtained as followed. HPLC columns: Waters Xterra® MS C$_8$ column 50 mm×4.6 mm at a flow of 2 mL/min for conditions A and B. Waters Xterra® MS C$_8$ column 150 mm×4.6 mm at a flow of 1 mL/min for conditions C and D.

Conditions A: 8 min gradient from 0.1% TFA in H$_2$O to 0.07% TFA in CH$_3$CN.

Conditions B: 8 min gradient from 95% H$_2$O to 100% CH$_3$CN.

Conditions C: 20 min gradient from 95% H$_2$O to 100% CH$_3$CN.

Conditions D: 20 min gradient from 95% H$_2$O to 40% CH$_3$CN. UV detection (maxplot) for all conditions.

The preparative HPLC were obtained with a Waters Xterra® Prep MS C$_8$ 10 μm column 300 mm×30 mm; UV detection (254 nM and 220 nM); flow: 30 mL/min. The MS data provided in the examples described below were obtained as followed: Mass spectrum: LC/MS Waters ZMD (ESI). The NMR data provided in the examples described below were obtained as followed: $^1$H-NMR: Bruker DPX-300 MHz.

According to a further general process, compounds of Formula (I) can be converted to alternative compounds of Formula (I), employing suitable interconversion techniques well known by a person skilled in the art.

If the above set of general synthetic methods are not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substitutents of each molecule and upon the ready availability of intermediates necessary; again such factors being appreciated by those of ordinary skill in the art. For all the protection and deprotection methods, see Kocienski, in "*Protecting Groups*", Georg Thieme Verlag Stuttgart, New York, 1994 and, Greene and Wuts in "*Protective Groups in Organic Synthesis*", Wiley Interscience, 3$^{rd}$ Edition 1999. Those skilled in the art will recognize that certain reactions are best carried out when potentially reactive functionality on the molecule is masked or protected, thus avoiding side reactions and/or increasing the yield of the reaction. Examples of protecting group moieties may be found in Kocienski, 1994 above and in Greene et al., 1999, above. The need and choice of protecting groups for a particular reaction is known to those skilled in the art and depends on the nature of the functional group to be protected (hydroxy, amino, carboxy, etc.), the structure and the stability of the molecule of which the substituent is part of the reaction conditions.

Compounds of this invention can be isolated or purified in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

The Following Reagents/Resins Commercially Available were Used:

2,2-dimethoxypropane (from Fluka), copper (II) chloride (from Aldrich), HOBt (from Aldrich), EDC (from Aldrich), 1-(4-fluorophenyl)piperazine dihydrochloride (from Aldrich), (R)-(−)-2-methylpiperazine (from Astatech), 1-bromo-4-(trifluoromethoxy)benzene (from Aldrich), 4-bromobiphenyl (from Fluka), 2,2'-bis(diphenylphosphino)-1,1'-binaphthalene (from Fluka).

Intermediate 1:
(3R)-1-biphenyl-4-yl-3-methyl-piperazine

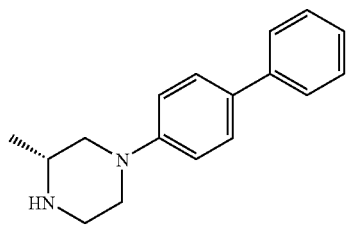

Toluene (700.00 mL) was degassed with nitrogen for 30 min. (R)-2-methylpiperazine (30.0 g; 299.5 mmol; 1.0 eq.), 4-bromophenyl (73.3 g; 314.5 mmol; 1.05 eq.), tBuONa (43.18 g; 449.3 mmol; 1.5 eq.), palladium (II) acetate trimer (3.36 g; 15.0 mmol; 0.05 eq.) and (+/−)-2,2'-bis(diphenylphosphino)-1,1'-binaphthalene (7.46 g; 12 mmol; 0.04 eq.) were added to the solution and the whole was heated at reflux over night. The reaction mixture was filtered first and Et$_2$O was added to the filtrates to precipitate the phosphine. Evaporation of the solvents gave a dark solid (133 g). Purification by preparative chromatography (800 g silica; DCM:

MeOH 90:10) gave dark solid. This solid was poured in Et₂O and a minimum amount of DCM was added to complete dissolution. Activated charcoal was added and the resulting mixture was stirred 30 min at RT. Filtration on a bed of cellite, evaporation of the solvents until a white prepcipate of an off-white powder. The mixture was chilled at −20° C. and the product was obtained by filtration. This solid was rinsed with cold (0° C.) Et₂O and dried under reduced pressure at 45° C. to give a first crop of the title compound as a white powder (17.3 g). The crystallization is repeated on the mother liquids to afford a second crop of white solid (13.8 g, 41% total yield). M⁺ (ESI): 253.3. ¹H NMR (CDCl₃, 300 MHz) δ 7.47 (d, J=7.3 Hz, 2H), 7.43 (d, J=8.7 Hz, 2H), 7.32 (t, J=7.6 Hz, 2H), 7.19 (t, J=8.2 Hz, 1H), 6.91 (d, J=8.7 Hz, 2H), 3.49 (d, J=11.9 Hz, 2H), 2.89-3.06 (m, 3H), 2.66 (td, J=11.4, 3.5 Hz, 1H), 2.31 (t, J=10.6 Hz, 1H), 1.06 (d, J=6.2 Hz, 3H). HPLC (Condition A): Rt: 2.5 min (HPLC purity: 98.5%).

Intermediate 2: (3R)-3-methyl-1-(4-trifluoromethoxyphenyl)-piperazine

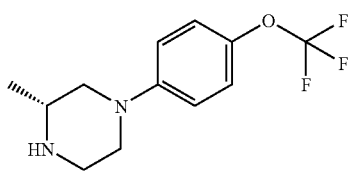

To a mixture of (R)-2-methylpiperazine (3.0 g, 30 mmol), 4-trifluoromethoxy bromo benzene (6.6 g, 27.5 mmol) and sodium tert-butoxide (3.56 g, 37.5 mmol) in dry toluene (50 mL) under nitrogen atmosphere, were added Pd(OAc)₂ (0.28 g, 12.5 mmol) followed by BINAP (0.62 g, 1 mmol) and refluxed for 16 h. Then the reaction mixture was concentrated and the crude compound was purified by column chromatography on silica gel using chloroform and methanol as eluent to give the title compound as a dark brown liquid (3 g, 38%).

EXAMPLE 1

(2R)₄-[4-(4-fluorophenyl)piperazin-1-yl]-N,2-dihydroxy-4-oxo butanamide (1)

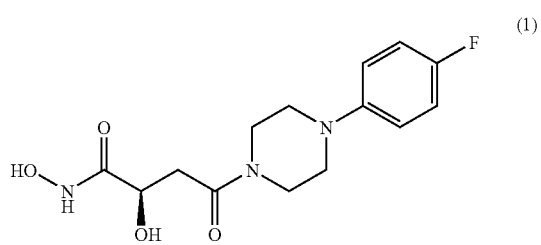

Step a) Formation of (5R)-5-{2-[4-(4-fluorophenyl) piperazin-1-yl]-2-oxoethyl}-2,2-dimethyl-1,3-dioxolan-4-one

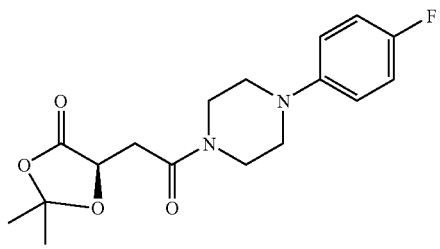

To a solution of [(4R)-2,2-dimethyl-5-oxo-1,3-dioxolan-4-yl]acetic acid (3.48 g; 20.0 mmol; 1.0 eq.), TEA (6.07 g; 60.0 mmol; 3.0 eq.) in DCM (60 mL) was added HOBt (2.97 g; 22.0 mmol; 1.1 eq.) and the mixture was chilled to 0° C. EDC (4.6 g; 24.0 mmol; 1.2 eq.) was then added and the resulting reaction mixture was stirred for 15 min at 0° C. 1-(4-fluorophenyl)piperazine dihydrochloride (5.57 g; 22.0 mmol; 1.1 eq.) was added and the resulting reaction mixture was stirred at RT over night. Purification by flash chromatography (AcOEt/c-Hex: 50/50) gave the title compound as a colorless oil (5.12 g, 76%). M⁺ (ESI): 337.2. HPLC (Condition A): Rt: 2.5 min (HPLC purity: 97.4%).

Step b) Formation of (2R)-4-[4-(4-fluorophenyl) piperazin-1-yl]-N,2-dihydroxy-4-oxobutanamide (1)

To a solution of (5R)-5-{2-[4-(4-fluorophenyl)-1-piperazinyl]-2-oxoethyl}-2,2-dimethyl-1,3-dioxolan-4-one (336 mg; 1.0 mmol; 1.0 eq.) in i-PrOH/THF (25/75) (5 mL) wad added an aqueous solution of hydroxylamine (50%, 0.295 mL; 5.0 mmol; 5.0 eq.). After stirring 3 h at RT, the solvents were evaporated to give a solid. This solid was crystallized from AcOEt (by addition of Et₂O and c-Hex) to give the title compound as a white powder (250 mg, 80%). M⁺ (ESI): 312.1; M⁻ (ESI): 310.1. ¹H NMR (DMSO-d₆, 300 MHz) δ 10.50 (s, 1H), 8.72 (s, 1H), 7.12-6.91 (m, 4H), 5.46 (d, J=3.0 Hz, 1H), 4.28 (q, J=6.3 Hz, 1H), 3.60 (s, 4H), 3.14-2.95 (m, 4H), 2.65 (d, J=6.3 Hz, 2H). HPLC (Condition A): Rt: 1.6 min (HPLC purity: 85.6%).

EXAMPLE 2

(2S)₄-[4-(4-fluorophenyl)piperazin-1-yl]-N,2-dihydroxy-4-oxobutanamide (2)

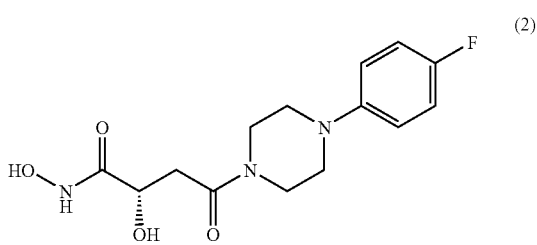

Step a) Formation of (5S)-5-{2-[4-(4-fluorophenyl) piperazin-1-yl]-2-oxoethyl}-2,2-dimethyl-1,3-dioxolan-4-one

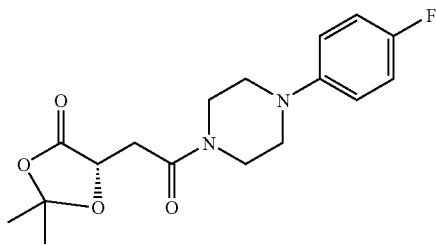

The title product was prepared following the procedure for the preparation of Example 1 (step a), but starting from [(4S)-2,2-dimethyl-5-oxo-1,3-dioxolan-4-yl]acetic acid (300 mg; 1.72 mmol; 1.0 eq.) to give the title compound as a white foam (350 mg, 60%). M⁺ (ESI): 337.1. $^1$H NMR (CDCl$_3$, 300 MHz) δ 7.12-6.83 (m, 4H), 4.94 (dd, J=3.0 Hz, J=7.5 Hz, 1H), 3.90-3.68 (m, 2H), 3.70-3.57 (m, 2H), 3.19-3.08 (m, 4H), 3.05 (dd, J=3.0 Hz, J=16.6 Hz, 1H), 2.85 (dd, J=7.5 Hz, J=16.6 Hz, 1H), 1.68 (s, 3H), 1.63 (s, 3H). HPLC (Condition A): Rt: 2.6 min (HPLC purity: 96.9%).

Step b) Formation of (2S)-4-[4-(4-fluorophenyl)piperazin-1-yl]-N,2-dihydroxy-4-oxo butanamide (2)

The title product was prepared following the procedure for the preparation of Example 1 (step b), but starting from (5S)-5-{2-[4-(4-fluorophenyl)piperazin-1-yl]-2-oxoethyl}-2,2-dimethyl-1,3-dioxolan-4-one (343 mg, 1.02 mmol) to give the title compound as a white powder (220 mg, 69%). M⁺ (ESI): 312.1; M⁻ (ESI): 310.0. $^1$H NMR (DMSO-d$_6$, 300 MHz) δ 10.53 (s, 1H), 8.75 (s, 1H), 7.18-6.85 (m, 4H), 5.47 (d, J=3.0 Hz, 1H), 4.28 (q, J=6.2 Hz, 1H), 3.60 (s, 4H), 3.16-2.93 (m, 4H), 2.65 (d, J=6.3 Hz, 2H). HPLC (Condition A): Rt: 1.2 min (HPLC purity: 93.2%).

EXAMPLE 3

(2S)—N,2-dihydroxy-4-{(2R)-2-methyl-4-[4-(trifluoromethoxy)phenyl]piperazin-1-yl}-4-oxobutanamide (3)

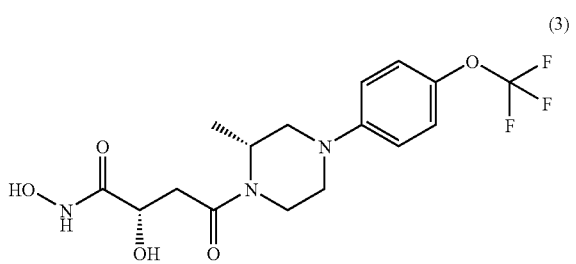

(3)

Step a) Formation of (5S)-2,2-dimethyl-5-[2-((2R)-2-methyl-4-{4-[(trifluoromethyl)oxy]phenyl}piperazin-1-yl)-2-oxoethyl]-1,3-dioxolan-4-one

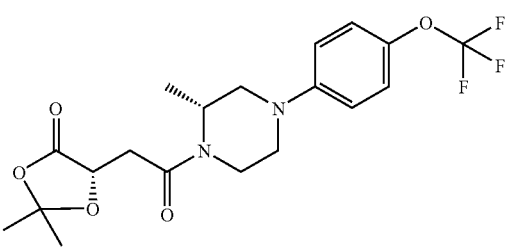

The title product was prepared following the procedure for the preparation of Example 1 (step a), but starting from [(4S)-2,2-dimethyl-5-oxo-1,3-dioxolan-4-yl]acetic acid (150 mg; 0.86 mmol; 1.0 eq.) and (3R)-3-methyl-1-{4-[(trifluoromethyl) oxy]phenyl}piperazine (Intermediate 2, 247 mg, 0.95 mmol, 1.1 eq.) to give the title compound as a colorless oil (123 mg, 34%). M⁺ (ESI): 417.2. $^1$H NMR (DMSO-d$_6$, 300 MHz) δ 7.05 (d, J=8.3 Hz, 2H), 6.79 (d, J=9.0 Hz), 4.91-4.74 (m, 1H), 4.91-4.74 (m, 1H), 4.51-4.39 (m, 0.5H), 4.11-3.95 (m, 0.5H), 3.68-3.21 (m, 3H), 3.16-2.55 (m, 4H), 1.57 (s, 3H), 1.51 (s, 3H), 1.40-1.20 (m, 3H). PLC (Condition A): Rt: 4.3 min (HPLC purity: 97.2%).

Step b) Formation of (2S)—N,2-dihydroxy-4-{(2R)-2-methyl-4-[4-(trifluoromethoxy)phenyl]piperazin-1-yl}-4-oxobutanamide (3)

The title product was prepared following the procedure for the preparation of Example 1 (step b), but starting from (5S)-2,2-dimethyl-5-[2-((2R)-2-methyl-4-{4-[(trifluoromethyl) oxy]phenyl}piperazin-1-yl)-2-oxoethyl]-1,3-dioxolan-4-one (117 mg, 0.28 mmol) to give the title compound as a white powder (81 mg, 74%). M⁺ (ESI): 392.2; M⁻ (ESI): 390.2. PLC (Condition A): Rt: 3.0 min (HPLC purity: 93.8%).

EXAMPLE 4

(2S)-4-[(2R)-4-biphenyl-4-yl-2-methylpiperazin-1-yl]-N,2-dihydroxy-4-oxobutanamide (4)

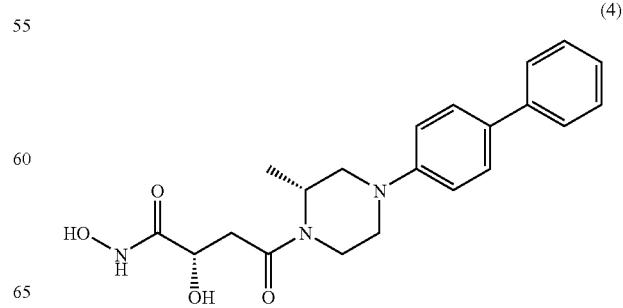

(4)

Step a) Formation of (5S)-5-{2-[(2R)-4-biphenyl-4-yl-2-methylpiperazin-1-yl]-2-oxoethyl}-2,2-dimethyl-1,3-dioxolan-4-one

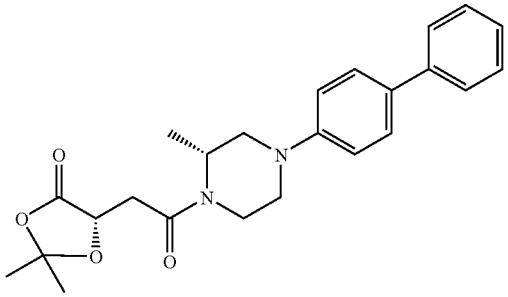

The title product was prepared following the procedure for the preparation of Example 1 (step a), but starting from [(4S)-2,2-dimethyl-5-oxo-1,3-dioxolan-4-yl]acetic acid (150 mg; 0.86 mmol; 1.0 eq.) and (3R)-1-biphenyl-4-yl-3-methyl piperazine (Intermediate 1, 239 mg, 0.95 mmol, 1.1 eq.) as a colorless oil (107 mg, 30%). M$^+$ (ESI): 409.3. HPLC (Condition A): Rt: 4.3 min (HPLC purity: 98.1%).

Step b) Formation of (2S)-4-[(2R)-4-biphenyl-4-yl-2-methylpiperazin-1-yl]-N,2-dihydroxy-4-oxobutanamide (4)

The title product was prepared following the procedure for the preparation of Example 1 (step b), but starting from (5S)-5-{2-[(2R)-4-biphenyl-4-yl-2-methylpiperazin-1-yl]-2-oxoethyl}-2,2-dimethyl-1,3-dioxolan-4-one (90 mg, 0.22 mmol). Purification of the crude product by reverse phase chromatography gave the title product as a white powder (60 mg, 71%). M$^+$ (ESI): 384.2; M$^-$ (ESI): 382.2. HPLC (Condition A): Rt: 3.0 min (HPLC purity: 99.0%).

Biological Assays:

The compounds of the present invention may be subjected to the following assays:

EXAMPLE 5

Enzyme Inhibition Assays

Compounds of the invention were tested to assess their activities as inhibitors of MMP-1, MMP-2, MMP-9 and MMP-12.

MMP-9 Assay Protocol

Compounds of the invention were tested for inhibitory activity against 92 kDa gelatinase (MMP-9) in an assay using a coumarin-labeled peptide substrate, (7-methoxycoumarin-4-yl)acetyl-Pro-Leu-Gly-Leu-(3-[2,4-dinitrophenyl]-L-2, 3diaminopropionyl)-Ala-Arg-NH2 (McaPLGLDpaAR) (Knight et al, 1992, *FEBS Lett.*, 263-266).

Stock solutions were made up as follows: Assay Butter: 100 mM Tris-HCl pH 7.6 containing 100 mM NaCl, 10 mM CaCl$_2$, and 0.05% Brij 35.

Substrate: 0.4 mM McaPLGLDpaAR (from Bachem) (0.437 mg/ml) stock solution in 100% DMSO (stored at −20° C.). Dilute to 8 μM in assay butter.

Enzyme: Recombinant human 92 kDa gelatinase (MMP-9; APMA (4-aminophenyl mercuric acetate)-activated if necessary appropriately diluted in assay butter.

Test Compounds were prepared initially as 10 mM compound solution in 100% DMSO, diluted to 1 mM in 100% DMSO, then serially diluted 3-fold in 100% DMSO across columns 1-10 of a 96-well microtitre plate Assay concentration range, 100 μM (column 1) to 5.1 μM (column 10).

The assay was performed in a total volume of 100 μL per well in 96-well microtitre plates. Activated enzyme (20 μL) was added to the wells followed by 20 μL of assay butter. Appropriate concentrations of test compounds dissolved in 10 μL of DMSO were then added followed by 50 μL of McaPLGLDpaAR (8 μM, prepared by dilution of DMSO stock in assay butter). For each as say ten concentrations of test compound were examined in duplicate. Control wells lack either enzyme or test compound. The reactions were incubated at 37° C. for 2 hours. The fluorescence at 405 nm was measured immediately with an SLT Fluostar fluorometer (SL T Labinstruments GmbH, Grödig, Austria) using 320 nm excitation, without stopping the reaction.

The effect of the test compound was determined from the dose response curve generated by the 10 duplicate concentrations of inhibitor. The IC$_{50}$ (the concentration of compound required to give a 50% decrease in enzyme activity) was obtained by fitting data to the equation, $Y=a+((b-a)/(1+(c/X)^d))$. (Y=inhibition achieved for a particular dose; X=the dose in nM; a=minimum y or zero % inhibition; b=maximum y or 100% inhibition; c=is the IC$_{50}$; d=is the slope). The result was rounded to one significant figure.

MMP-12 Assay Protocol

Compounds of the invention were tested for inhibitory activity against metalloelastase (MMP-12) in an assay using a coumarin-labelled peptide substrate, (7-methoxycoumarin-4-yl)acetyl-Pro-Leu-Gly-Leu-(3-[2,4-dinitrophenyl]-L-2,3-diaminopropionyl)-Ala-Arg-NH2 (McaPLGLDpaAR) (Knight et al, 1992, above). The protocol for this assay was as described for the MMP-9 assay above.

MMP-1 Assay Protocol

Compounds of the invention were tested for inhibitory activity against collagenase (MMP-1) in an assay using a coumarin-labelled peptide substrate, (7-methoxycoumarin-4-yl)acetyl-Pro-Leu-Gly-Leu-(3-[2,4-dinitrophenyl]-L-2, 3diaminopropionyl)-Ala-Arg-NH2 (Mca PLGLDpaAR) (Knight et al, 1992, above). The protocol for this assay was as described for the MMP-9 assay above.

MMP-2 Assay Protocol

Compounds of the invention were tested for inhibitory activity against gelatinase A (MMP-2) in an assay using a coumarin-labelled peptide substrate, (7-methoxycoumarin-4-yl)acetyl-Pro-Leu-Gly-Leu-(3-[2,4-dinitrophenyl]-L-2, 3diaminopropionyl)-Ala-Arg-NH2 (Mca PLGLDpaAR) (Knight et al, 1992, above). The protocol for this assay was as described for the MMP-9 assay above.

The results are expressed in terms of IC$_{50}$ (the concentration of compound required to give a 50% decrease in enzyme activity) and are presented in Table 1 below for compounds of Formula (I).

TABLE 1

| | IC$_{50}$ on different MMPs: | |
| --- | --- | --- |
| Example | MMP-1 IC$_{50}$ (nM) | MMP-12 IC$_{50}$ (nM) |
| Example 1 | >5000 | 264 |
| Example 2 | >5000 | 58 |
| Example 3 | >5000 | 5 |
| Example 4 | >5000 | 5 |

EXAMPLE 6

IL-2-Induced Peritoneal Recruitment of Lymphocytes

Administration of IL-2 intraperitoneally causes migration of lymphocytes into the intraperitoneal cavity. This is a model for the cellular migration that occurs during inflammation.

Protocol

C3H/HEN mice (Elevage Janvier, France) are intraperitoneally injected with IL-2 (Serono Pharmaceutical Research Institute, 20 µg/kg, in saline).

Compounds of the invention are suspended in 0.5% carboxymethylcellulose (CMC)/0.25% tween-20 and are administered by s.c. or p.o. route (10 ml/kg) 15 min prior to administration of IL-2.

Twenty-four hours after administration of IL-2, peritoneal white blood cells are collected by 3 successive lavages of the peritoneal cavity with 5 ml phosphate buffered saline (PBS)-1 mM EDTA (+4° C.). The suspension is centrifuged (1700 g×10 min at +4° C.). The resulting pellet is suspended in 1 ml PBS-1 mM EDTA.

Lymphocytes are identified and counted using a Beckman/Coulter counter.

Experimental Design

The animals are divided into 6 groups (6 mice each group):

Group 1: (baseline) receives 0.5% CMC/0.25% tween-20 (vehicle of compound of the invention) and saline (vehicle of IL-2);

Group 2: (control IL-2) receives 0.5% CMC/0.25% tween-20 and injection of IL-2;

Group 3: Experimental group (Compound of the invention Dose 1) receives a compound of the invention and injection of IL-2;

Group 4: Experimental group (Compound of the invention Dose 2) receives a compound of the invention and injection of IL-2;

Group 5: Experimental group (Compound of the invention Dose 3) receives a compound of the invention and injection of IL-2;

Group 6: Reference group receives reference compound dexamethasone and injection of IL-2.

Calculation

Inhibition of lymphocyte recruitment is calculated as follows:

$$\% \text{ inhibition} = \frac{1 - (LyX - Ly1)}{(Ly2 - Ly1)} \times 100\%$$

Where Ly 1=Number of lymphocytes in group 1 (E3 µl), Ly 2=Number of lymphocytes in group 2 (E3 µl), Ly X=Number of lymphocytes in group X (3-5) (E3 µl).

The results for compounds according to Formula (I) are presented in Table 2 below.

TABLE 2

Percentage of inhibition of IL-2-induced peritoneal recruitment of lymphocytes by compounds of the invention:

| Example | Dose (mg/kg) | Route | % inhibition |
|---|---|---|---|
| Example 2 | 1 | po | 51 |

EXAMPLE 7

Chronic Obstructive Pulmonary Disease (COPD) Model

Compounds of the invention can be evaluated for their ability to prevent cigarette smoke-induced COPD.

Female AJ mice (Harlan, 17-25 g) are exposed daily to cigarette smoke (CS) for 11 consecutive days in groups of 5, in individual clear chambers. Animals are weighed prior to treatment, on day 6 of exposure and on day 12. The CS was generated using IR1 cigarettes purchased from the Institute of Tobacco Research, University of Kentucky, USA and is allowed to enter the chambers at a flow rate of 100 ml/min.

In order to minimise any potential problems caused by repeated exposure to a high level of daily CS, the exposure of the mice to TS is increased gradually over the time to a maximum of 6 cigarettes from day 5 to day 11 (approximately 48 min exposure).

A sham group of mice is also exposed to air on a daily basis for equivalent lengths of time as controls (no CS exposure).

Treatment

Compounds of the invention are prepared in 0.5% carboxymethylcellulose Na salt (CMC, Sigma reference C-4888) as vehicle.

Animals are orally dosed twice daily by gavage in a dose volume of 5 ml/kg, 1 h prior to air or CS exposure and 6 h after the cessation of the exposure.

Sham animals (n=10) received vehicle and are exposed to air for up to a maximum of 50 minutes per day. The control group (n=10) received vehicle and is exposed to CS (up to a maximum of 6 cigarettes per day). Additional groups are exposed to CS (from up to a maximum of 6 cigarettes per day) and treated with one of the test compounds or the reference compound.

Bronchoalveolar Lavage and Cytospin Analysis

Twenty-four hours after the last CS exposure, bronchoalveolar lavage is performed as follows:

The trachea is dissected under deep anesthesia (sodium pentobarbitone) and cannulated using a Portex nylon intravenous cannula shortened to approximately 8 mm. Phosphate buffered saline (PBS, Gibco) containing 10 units/ml heparin (0.4 ml) is gently instilled and withdrawn 3 times. The lavage fluid is placed in an Eppendorf tube and kept on ice prior to subsequent determinations. Then, lavage fluid is separated from cells by centrifugation. The supernatant is removed and frozen for subsequent analysis. The cell pellet is resuspended in PBS and total cell numbers are calculated by counting a stained aliquot (Turks stain) under a microscope using a haemocytometer.

Differential cell count is then performed as follows: The residual cell pellet is diluted to approximately 105 cells per ml. A volume of 500 µl is placed in the funnel of a cytospin slide and is centrifuged for 8 min at 800 rpm. The slide is air-dried and stained using 'Kwik-Diff' solutions (Shandon) following purchaser instructions. Slides are dried and cover-slipped and differential cell count is done using light microscopy. Up to 400 cells are counted for each slide. Cells were differentiated using standard morphometric techniques.

Statistical Analysis

The mean+/−S.D. is calculated for each experimental group.

Results are analyzed using a one-way analysis of variance (ANOVA), followed by a Bonferroni correction for multiple comparisons. Statistical significance is considered with $p<0.05$.

EXAMPLE 8

Experimental Allergic Encephalomyelitis (EAE) Model

Compounds according to the invention can be evaluated for their activity in a model for multiple sclerosis in mice.

Animals

C57BL/6NCrlBR female mice are used. Mice are kept in wire cages (cm 32×14×13 h) with stainless steel feeders and fed on a standard diet (4RF21, Charles River, Italy) and water ad libitum. From day 7, wet pellets are also placed every day on the bottom of the cage. Plastic bottles are used in addition to the automatic water system.

Experimental Procedure

Mice are immunized (day=0) by injecting s.c. in the left flank 0.2 ml of an emulsion composed of 200 µg $MOG_{35-55}$ peptide (Neosystem, Strasbourg, France) in Complete Freund's Adjuvant (CFA, Difco, Detroit, U.S.A.) containing 0.5 mg of *Mycobacterium tuberculosis*. Immediately after, they receive an i.p. injection of 500 ng pertussis toxin (List Biological Lab., Campbell, Calif., U.S.A.) dissolved in 400 µL of buffer (0.5 M NaCl, 0.017% Triton X-100, 0.015 M Tris, pH=7.5). On day 2, the animals are given a second injection of 500 ng pertussis toxin.

On day 7, the mice receive a second dose of 200 µg of $MOG_{35-55}$ peptide in CFA injected s.c. in the right flank. Starting approximately from day 8-10, this procedure results in a progressing paralysis, arising from the tail and ascending up to the forelimbs.

Animals are individually weighed and are examined for the presence of paralysis that is scored according to the following score-system:

0=no signs of disease 0.5=partial tail paralysis

1=tail paralysis 1.5=tail paralysis+partial unilateral hindlimb paralysis

2=tail paralysis+bilateral hindlimb weakness or partial paralysis 2.5=tail paralysis+partial hindlimb paralysis (lowered pelvi)

3=tail paralysis+complete hindlimb paralysis 3.5=tail paralysis+hindlimb paralysis+incontinence 4=tail paralysis+hindlimb paralysis+weakness or partial paralysis of forelimbs 5=moribund or dead Mortality and clinical signs are monitored daily in each group of treatment, by a technician who is unaware of treatments.

Daily treatment with compounds, their vehicle or with a reference compound starts on day 7 and continued for 15 or 21 consecutive days in all groups.

Histopathological Examination

At the end of the treatment period, each animal is anesthetised with sodium pentobarbital and is transcardially perfused-fixed with 4% paraformaldehyde via the left ventricle. Fixed spinal cords are then carefully dissected out.

Spinal cord slices are embedded in paraffin blocks. Sectioning and staining with hematoxylin and eosin and CD45 staining for inflammation, and with Kluver-PAS (Luxol fast blue plus Periodic Acid Schiff staining) and Bielchowski's staining for the detection of demyelination and axonal loss, are performed.

In the spinal cord, the total area of all slices is measured for each animal as points of intersection of a 10×10 grid at a magnification of 0.4×0.4 mm per grid. The perivascular inflammatory infiltrates are counted in each slice in order to obtain a total value for each animal and evaluated as number of infiltrates per $mm^2$. Demyelination and axonal loss areas are measured for each animal as points of intersection of 10×10 grid at a magnification of 0.1×0.1 mm per grid and are expressed as a percentage of total demyelination area over the total area of the slices.

Data Evaluation and Statistical Analysis

The results of clinical and histopathological observations are expressed as the mean (±SEM) scores in each treatment group. Values obtained in the test drug-treated groups are compared with that of the positive control group. Significance of differences among groups relating to clinical score are analysed by one-way ANOVA, followed in case of significance (p<0.05) by Fisher test.

Differences among groups for the presence of perivascular inflammatory infiltrates and the extent of demyelination and axonal loss in the spinal cord as well as body weight data are analysed by one-way ANOVA, followed in case of significance (p<0.05) by Fisher test.

EXAMPLE 9

Preparation of a Pharmaceutical Formulation

The following formulation examples illustrate representative pharmaceutical compositions according to the present invention being not restricted thereto.

Formulation 1—Tablets

A compound of the invention is admixed as a dry powder with a dry gelatin binder in an approximate 1:2 weight ration. A minor amount of magnesium stearate is added as a lubricant. The mixture is formed into 240-270 mg tablets (80-90 mg) of active N-hydroxyamide derivative per tablet) in a tablet press.

Formulation 2—Capsules

A compound of the invention is admixed as a dry powder with a starch diluent in an approximate 1:1 weight ratio. The mixture is filled into 250 mg capsules (125 mg of active N-hydroxyamide derivative per capsule).

Formulation 3—Liquid

A compound of the invention (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active N-hydroxyamide derivative) in a tablet press.

Formulation 5—Injection

A compound of the invention is dissolved in a buffered sterile saline injectable aqueous medium to a concentration of approximately 5 mg/ml.

The invention claimed is:

1. An N-hydroxyamide derivative according to Formula (I),

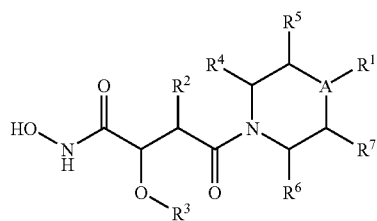

wherein:

A is N;

$R^1$ is aryl, optionally substituted with halogen or —O—R;

R is $C_1$-$C_6$ alkyl, optionally substituted with halogen, $R^2$ is H;

$R^3$ is H;

$R^4$ is selected from H and unsubstituted $C_1$-$C_6$ alkyl; and $R^5$, $R^6$ and $R^7$ are H;

or an enantiomer, diastereomer, racemate, or a pharmaceutically acceptable salt thereof.

2. An N-hydroxyamide derivative according to claim 1 wherein $R^1$ is phenyl.

3. An N-hydroxyamide derivative according to claim 1, selected from the group consisting of:

(2R)-4-[4-(4-fluorophenyl)piperazin-1-yl]-N,2-dihydroxy-4-oxobutanamide;

(2S)-4-[4-(4-fluorophenyl)piperazin-1-yl]-N,2-dihydroxy-4-oxobutanamide;

(2S)—N,2-dihydroxy-4-{(2R)-2-methyl-4-[4-(trifluoromethoxy)phenyl]piperazin-1-yl}-4-oxobutanamide; and (2S)-4-[(2R)-4-biphenyl-4-yl-2-methylpiperazin-1-yl]-N,2-dihydroxy-4-oxo butanamide;

or a pharmaceutically acceptable salt thereof.

4. A method of treating a subject with a matrix metalloproteinase (MMP) associated disease or disorder, wherein the metalloproteinase is selected from the group consisting of MMP-9, MMP-2 and MMP-12, and the disease or disorder is associated with MMP activity and/or expression, and the matrix metalloproteinase (MMP) associated disease or disorder is multiple sclerosis or chronic obstructive pulmonary disorders, comprising administering to the subject an effective amount of a compound according to claim 1.

5. A pharmaceutical composition comprising a compound according to claim 1 and a pharmaceutically acceptable carrier, diluent or excipient thereof.

6. A process for the manufacture of a compound of formula I:

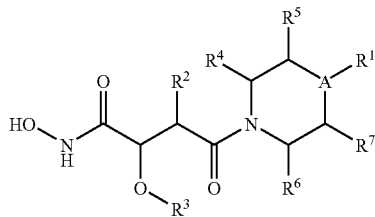

said process comprising the step of reacting a compound of Formula (IV):

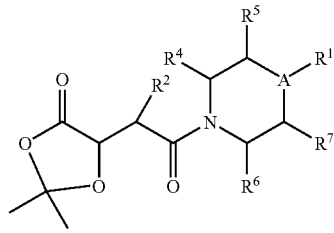

with a hydroxylamine, $H_2NO$—$R^8$, and thereby forming the compound according to Formula I;

wherein

A is N;

$R^1$ is aryl, optionally substituted with halogen or —O—R;

R is $C_1$-$C_6$ alkyl, optionally substituted with halogen;

$R^2$ is H;

$R^4$ is selected from H and unsubstituted $C_1$-$C_6$ alkyl;

$R^5$, $R^6$ and $R^7$ are H; and $R^8$ is selected from H, t-butyl, benzyl, trialkylsilyl, and tetrahydropyranyl.

7. The process according to claim 6, further comprising a deprotection step, wherein the deprotection step is occurring at $R^8$, when $R^8$ is not H.

8. A compound according to Formula (IV):

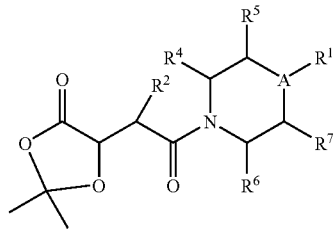

wherein

A is N;

$R^1$ is aryl, optionally substituted with halogen or —O—R;

R is $C_1$-$C_6$ alkyl, optionally substituted with halogen;

$R^2$ is H; and $R^4$ is selected from H and unsubstituted $C_1$-$C_6$ alkyl; and $R^5$, $R^6$ and $R^7$ are H;

or a pharmaceutically acceptable salt thereof.

9. A compound according to claim 8 selected from the group:

(5R)-5-{2-[4-(4-fluorophenyl)piperazin-1-yl]-2-oxoethyl}-2,2-dimethyl-1,3-dioxolan-4-one;

(5S)-5-{2-[4-(4-fluorophenyl)piperazin-1-yl]-2-oxoethyl}-2,2-dimethyl-1,3-dioxolan-4-one;

(5S)-2,2-dimethyl-5-[2-[((2R)-2-methyl-4-{4-[(trifluoromethyl)oxy]phenyl}piperazin-1-yl)-2-oxoethyl]-1,3-dioxolan-4-one; and (5S)-5-{2-[(2R)-4-biphenyl-4-yl-2-methylpiperazin-1-yl]-2-oxoethyl}-2,2-dimethyl-1,3-dioxolan-4-one;

or a pharmaceutically acceptable salt thereof.

* * * * *